United States Patent

Resul

Patent Number: 5,359,095
Date of Patent: Oct. 25, 1994

[54] METHOD FOR SYNTHESIS OF PROSTAGLANDIN DERIVATIVES

[75] Inventor: Bahram Resul, Uppsala, Sweden

[73] Assignee: Pharmacia AB, Uppsala, Sweden

[21] Appl. No.: 193,525

[22] Filed: Feb. 8, 1994

Related U.S. Application Data

[63] Continuation of Ser. No. 838,811, Mar. 19, 1992, abandoned.

[30] Foreign Application Priority Data

Aug. 8, 1990 [SE] Sweden .......................... 9002596-6

[51] Int. Cl.⁵ ................. C07C 405/00; C07D 307/935
[52] U.S. Cl. .................................................... 549/305
[58] Field of Search ........................................ 549/305

[56] References Cited

U.S. PATENT DOCUMENTS 3,962,312  6/1976  Hayashi ............................... 562/465
4,036,832  7/1977  Hess ..................................... 549/415

Primary Examiner—C. Warren Ivy
Assistant Examiner—A. A. Owens
Attorney, Agent, or Firm—Fred Philpitt

[57] ABSTRACT

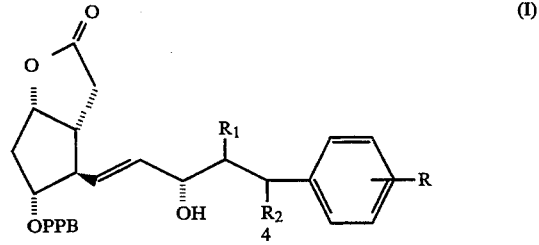

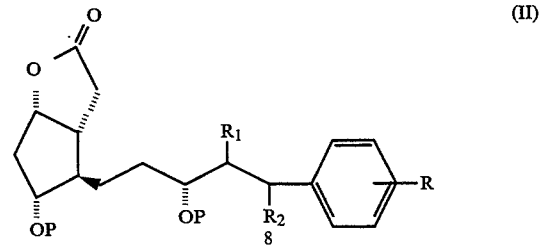

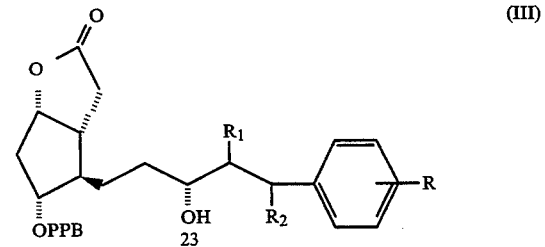

Method for preparing 13,14-dihydro-17-phenyl analogues of $PGF_{2\alpha}$ or $PGE_2$ comprising the step of hydrogenating the double bond in an intermediate compound (1) without deoxygenation of the allylic alcohol to give one of the intermediate compounds (II, III) wherein R is hydrogen or one or more halogen, hydroxyl, cyanide, alkyl (preferably 1-4 carbon atoms). hydroxyalkyl, trifluoromethyl or aromatic or heteroaromatic substituents on the aromatic ring $R_1$ and $R_2$ are each hydrogen alkyl (preferably 1-4 carbon atoms), hydroxyl, halogen or hydroxyalkyl substituents, $R_3$ is O-alkyl or N(alkyl), P is a protecting group.

2 Claims, No Drawings

METHOD FOR SYNTHESIS OF PROSTAGLANDIN DERIVATIVES

This is a continuation of application Ser. No. 07/838,811, filed Mar. 19, 1992 now abandoned, and the benefits of 35 USC 120 are claimed relative to it.

The invention is concerned with the synthesis of certain 13,14-dihydro prostaglandin analogues, and especially 13,14-dihydro-17-phenyl trinor analogues of prostaglandin E and F. The 17-phenyl PGF analogues, in particular, have earlier been found to exhibit ocular hypotensive activity with minimal ocular irritation and conjunctival hyperemia.

Prostaglandin derivatives have been found to be of great interest as agents for lowering the intraocular pressure, see for instance U.S. Pat. No. 4,599,353 (Bito), EP87103714.9 (Bito), EP344235 (Stjernschantz) and EP364417 (Stjernschantz). With respect to the practical usefulness of some of the prostaglandins and derivatives, as suitable drugs for treating glaucoma or ocular hypertension, a limiting factor is their property of causing superficial irritation and vasodilation in the conjunctiva. It is probable, moreover, that prostaglandins have an irritant effect on the sensory nerves of the cornea. Thus local side effects will arise in the eye already when the amounts of prostaglandin administered are quite small—that is, already when the doses are lower than those that would be desirable for achieving maximum pressure reduction. It has thus been found, for instance, that for this reason it is clinically impossible to use $PGF_{2\alpha}$-1-isopropyl ester in the amount that would give maximum pressure reduction. Prostaglandins, being naturally occurring auracolds, are very potent pharmacologically and affect both sensory nerves and smooth muscle of the blood vessels. Since the effects caused by administrations of $PGF2\alpha$ and its esters to the eye, comprise in addition to pressure reduction also irritation and hyperemia (increased blood flow), the doses currently practicable in clinical tests are necessarily very low. The irritation experienced when $PGF2\alpha$ or its esters are applied, consists mainly in a feeling of grittiness or of having a foreign body in one's eye, this being usually accompanied by increased lacrimation.

We have found, as described in PCT patent application WO90/02553, that a solution to the problems discussed above is the use of certain derivatives of prostaglandins for the Treatment of glaucoma or ocular hypertension. In these derivatives the omega chain has been modified with the common feature of containing an aromatic ring. Among the compounds disclosed in that patent application 13,14-dihydro PGF analogues, and especially 13,14-dihydro-17-phenyl trinor $PGF2\alpha$ analogues have been found to possess a high selectivity in lowering IOP without having the undesirable side effects.

The synthesis of these rather complicated molecules is complex and a considerable number of reactions are involved. It is therefore of great importance that besides giving a high yield, the desired compound should not contain intermediates and reagent residues to an extent that would cause undesired side effects in therapy. In accordance with this invention a convenient method has been developed for preparing 13,14-dihydro PGE and PGF analogues, and especially 13,14-dihydro-17-phenyl trinor analogues of prostaglandin $E_2$ and $F_{2\alpha}$. The method is illustrated by the reaction schemes I and II for preparing 13,14-dihydro-17-phenyl-18,19,20-trinor $PGE_2$ or $PGF_{2\alpha}$ esters or amides.

The following designations have been used in the reaction schemes as well as in description and claims:

R is hydrogen or one or more halogen, hydroxyl, cyanide, alkyl (pref. 1–4 carbon atoms), hydroxyalkyl trifluoromethyl, aromatic or heteroaromatic ring substituents on aromatic ring $R_1$ and $R_2$ are each hydrogen alkyl (pref 1–4 carbon atoms), hydroxyl, halogen or hydroxyalkyl substituents $R_3$ is O-alkyl or N(alkyl), and n is an integer, like in the range of from 1 to 10, preferably 1–5, and especially 1, 2 or 3.

P is a protecting group, for instance tetrahydropyran ether, trimethylsilyl ether, t-butyldimethylsilyl ether, p-phenylacetate ester, etc.

PPB stands for para-phenyl-benzoyl.

Other substituents giving functionally similar derivatives to be used for reducing intra ocular pressure but without causing undesired side-effects are of course within the scope of the present invention.

As used herein, the dotted line ( ... ) indicate that the substituents are in a configuration below the plane of the molecule, the triangular shape (▶) denotes the configuration above the plane of the molecule and a wavy line (∿) indicates a substituent which is above and below the plane of the molecule.

The reaction schemes are as mentioned above illustrated by the synthesis of isopropyl esters of PGF but it is readily appreciated that any structural analogue can be prepared according to this method. Such analogues include but is not limited to other alkyl esters or diestors as well as amides of PGF and PGE.

In the method of this invention for preparing 13,14-dihydro-17-phenyl PGF analogues a commercially available —(—) Coreys lactone (4), a bicyclic lactone corresponding to Formula 1 is used. The primary alcohol of lactone 1 is oxidised with a mild oxidizing agent to aldehyde 2 using a modified method described by Pfitzner Moffatt (5) using dicyclohexylcarbodiimide (DCC), dimethylsulfoxide (DMSO) and phosphoric acid in dimethoxyethane (DME), which is reacted further without isolation with dimethyl-2-oxo-4-phenyl-butylphosphonate using Emmon-Horner method to give 3, where upon the resulting crystalline $\alpha,\beta$-unsaturated ketone is reduced stereo-selectively with tri-sec-butylborohydride (6) (lithium selectride) at $-120°$ C. furnishing 70% S. Hydroxyl isomer over R-isomer; alternatively, sodium borohydride in the presence of cerium chloride (7) in methanol at $-78°$ C. reduce unsaturated ketone with lower selectivity, the epimers are separated by flash column chromatography on silicagel to give 4 in 50% yield. The phenylbenzoyl group is removed by basic hydrolysis using for instance potassium carbonate or sodium hydroxide in a suitable solvent, like methanol affording the compound 6. It has been found that the allylic alcohol in 4 is deoxygenated on hydrogenation of the double bond over palladium catalyst, and loss of oxygen occurs along with double bond saturation in about 30%. Therefore, it is necessary to protect the hydroxyl groups with a protecting group, for example tetrahydropyran, to give 7, which is reduced under hydrogen atmosphere using a catalysts, like Pd-C or Pt in a suitable solvent, like THF or ethanol to give the compound 8 in quantitative yield. The bistetrahydropyranyl ether is treated with diisobutylaluminiumhydride in toluene at $-78°$ C. to give lactol 9 in quantitative yield, followed by wittig reaction with (4-carboxybutyl)triphenylphosphonium-bromide and sodium methyl sulfinylmethide to afford the acid 10, which is reacted further without isolation with isopropyliodide and DBU to give ester corresponding to formula 11, which is isolated and treated with pyridinium-4-toluenesulfonate in ethanol to eliminate the tetrahydropyranyl protecting groups, afforded the final desired product 12.

The bistetrahydropyranyl ether 11 is treated with pyridinium chlorochromate adsorbed on aluminia (9) in dichloromethane to give the corresponding PGE analogue 21, which is isolated and treated with pyridinium-4-toluenesulfonate in ethanol to give 17-phenyl-18,19,20-trinor-PGE$_2$ ipr ester 22.

Deoxygenation can also be deminished greatly using an alkalimetal salt, for example sodium or potassium nitrite mixed with a catalysts like Pd-C or Pt in a suitable solvent Like ethanol. Compound 4 is preferably reduced under hydrogen atmosphere using Pd-C and 5% sodium nitrite in ethanol to give 23 in good yield. Compound 23 is isolated and reacted with diisobutylaluminiumhydride at $-70°$ C.-($-75$)° C. furnishing lactol 24 in good yield, which is reacted further without isolatation with potassium carbonate in methanol to give 25, which is purified by chromatography on silica gel using ethylacetate: acetone (4:1) as eluent, followed by witting reaction with 4-carboxylbutyl-triphenyl phosphonium bromide and sodium methyl sulfinylmethide furnishing prostaglandin acid 26, which is reacted further without isolation with isopropyl iodide and DBU to give a corresponding ester, which is chromatographed twice on silica gel using ethylacetate: chloroform (1:1) and isopropanol:isopropylether (1:3) to give a pure desired product.

The invention is accordingly concerned with a method for preparing 13,14-dihydro-17-phenyl-18-19-20 trinor PGE and PGF derivatives comprising the step of hydrogenating the double bond in an intermediate compound

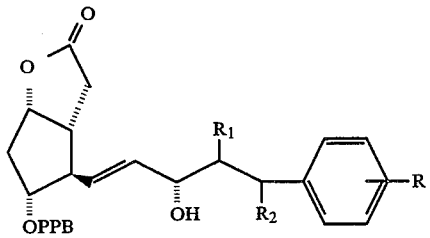

without deoxygenation of the allylic alcohol to give one of the intermediate compounds

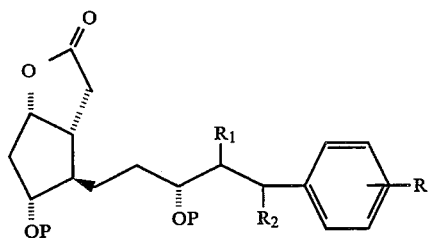

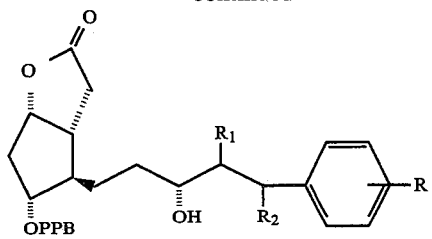

wherein R, R$_1$, R$_2$, R$_3$ and P have the definitions given above.

In a preferred embodiment of the invention the complete method is carried out according to one of the reaction schemes I or II.

The present invention is further illustrated by the following experiments. Reference is given to the general reaction schemes I and II, and in these specific compounds of the examples the substituents R$_1$, R$_2$ and R$_3$ are each hydrogen, R$_3$ is O-isopropyl, the phenyl ring is unsubstituted (R=H) and n=1.

Preparation of
3,14-dihydro-17-phenyl-18,19,20-trinor-PGF$_{2\alpha}$-isopropyl ester (scheme I)

Step a

Preparation of 1-(S)-2-oxa-3-oxo-6R-formyl-7R-(4-phenylbenzoyloxy)cis-bicyclo-[3,3,0]-octane 2:

A mixture of alcohol A (20 g, 56, 8 mmol), DCC (35,1 g, 170,0 mmol), DMSO (35,5 g, 454 mmol) and DME (80 ml) was stirred mechanically under nitrogene at ambient temperature for 5 min, and thereafter one portion of orthophosphoric acid 85% (3,3 g, 28,4 mmol) was added. After stirring for 2 h, at which time the reaction was complete (TLC monitoring), the resultant precipitate was filtered off and washed with DME to give the unstable crude aldehyde 2 R$_f$=0,32 (silicagel, EtoAc:toluene 2:1)

Step b

Preparation of 1-(S)-2-oxa-3-oxo-6R-[3-oxo-5-phenyl-1-transpentenyl]-7R-(4-phenylbenzoyloxy)-cis-bicyclo-[3,3,0]-octane 3:

To a suspension of NaH(2,2 g, 74 mmol) (80% washed with n-pentane to remove mineral oil) in DME (150 ml) under nitrogene, was added dropwise dimethyl-2-oxo-4-phenylbutylphosphonate (20,9 g,81,6 mmol) prepared according to the method described by Corey et al [8], in DME (50 ml) and stirred mechanically for 1 h at room temperature. The mixture was then cooled to $-10°$ C. and a solution of the crude aldehyde 2 was added dropwise. After 15 min at 0° C. and 1 h at room temperature (TLC monitoring) the reaction mixture was neutralized with glacial acetic acid, the solvent was removed and to the residue was added ethyl acetate (150 ml), washed with water (50 ml) and brine (50 ml). The organic layer was dried over unhydrous sodium sulfate. The solvent was Then removed in vacuo and the resulting white precipitate was filtered and washed with cold ether. The title compound 3 was a crystalling substance mp 134–135,5; yield=28 g (63%) ; R$_f$=0,55 (silicagel, EtoAc:toluene 2:1)
$[\alpha]_D^{20}$=116 (C=1,26 , CH$_3$CN)
$^1$H-NMR( CDCl$_3$/TMS): $\sigma$=2,9 (m, 8H), 5,1 (t, 1H), 5,3(9, 1H), 6,2(d, 1H), 6,7(dd, 1H), 7,1–7,6(m, 10H), 8,1(d, 4H)

Step c (two alternative methods A and B given)

Preparation of 1-(S)-2-oxa-3-oxo-6R-[3S-hydroxy-5-phenyl-1-trans-pentenyl]-7R-(4-phenylbenzoyloxy) cis-bicyclo-[3,3,0]-Octane 4:

Method A

To a stirred solution of tri-sec-butylborohydride (0,5 g, 13,55 mmol) in THF: ether (30 ml, 1:1) at −120° C. under nitrogen was added dropwise a solution of enone (5 g,10,325 mmol) cooled to −78° C. after 1 h (TLC monitoring). The reaction mixture was quenched by addition of saturated ammonium chloride. The temperature was raised to ±0° C., water was added, and the mixture transferred to a separatory funnel, diluted with ethylacetate (50 ml) and washed with brine (25 ml). The organic phase was dried ($Na_2So_4$), concentrated and subjected to flash column chromatography (silicagel, ethylacetate) furnishing 4 as a white crystalline product. yield 3 g (60%), $R_f$=0,5 (silicagel, EtoAc)

$[\alpha]^{D}_{25}$=−101,59 (C=0,69 $CH_3CN$) $^1$H-NMR($CDCl_3$/TMS ): $\sigma$=4,1 (9, 1H), 5,05 (m, 1H), 5,3 (9, 1H), 7,1–7,6(m, 10H), 8,1(d=4H)

Method B

To a stirred mixture enone (5 g, 10,3 mmol) and cerous chloride heptahydrate (1,55 g, 4 mmol) in methanol (30 ml) and dichloromethane (15 ml) at −78° C. under nitrogene was added sodium borohydride (0,24 g, 6,3 mmol) in small portions. After 30 min. (TLC monitoring) the reaction mixture was quenched by addition of saturated ammonium chloride, and extracted with ethyl acetate (50 ml), dried over unhydrous sodium sulfate, evaporated and subjected to flash chromatography (silicagel, ethylacetate) furnishing 4 as a white crystalline product m.p 128,2°–129° C. yield 1,7 g (37%).

Step d

Preparation of 1-(S)-2-oxa-3-oxo-6R-[3S-hydroxy-5-phenyl-1-trans-pentenyl]-7R-hydroxy-cis-bicyclo-[3,3,0]-octane 6:

To a solution of lactone 4 (9,8 g, 20,0 mmol) in methanol (100 ml) was added potassium caronate (1,7 g, 12 mmol), and stirred at ambient temperature for 3 h (TLC monitoring). The mixture was neutralized with 1N HCL (40 ml) and the product extracted with ethyl acetate (2×50 ml). The organic phase was dried ($Na_2SO_4$) and evaporated to dryness. The crude product was subjected to flash column chromatography (silicagel, ethylacetate: acetone 1:1). The title compound 6 was obtained as a colourless oil yield=4,9 g (85%)

$[\alpha]_D^{20}$= −20,48 (C=2,5 $CH_3CN$) $R_f$=0,31 (silicagel: EtoAc) $^1$H-NMR($CDCl_3$/TMS ): $\sigma$=1,9 (m, 2H), 2,7 (m, 4H), 3,9 (9, 1H), 4,1(m, 1H), 4,9 (m, 1H), 5,5 (m, 1H), 5,6 (m, 1H), 7,2 (m, 5H).

Step e

Preparation of 1(S)-2-oxa-3-oxo-6R-[3S-(2-tetrahydropyranyloxy)-5-phenyl-1-trans-pentenyl]-7R-(2-tetrahydropyranyloxy)-cis-bicyclo-[3,3,0]-octane 7:

To a stirred solution of alcohol 6 (3,3 g, 11,6 mmol) and dihydropyran (4,4 g, 52 mmol) in dichloromethane (50 ml) under nitrogene was added pyridinium-4-toluenesulfonate (0,3 g, 1,15 mmol). The mixture was allowed to stand at room temperature for 16 h (TLC monitoring), the solution was quenched with methanol (10 ml), and the solvent was removed in vacuo. The residue was diluted with ether (100 ml), transferred to a separatory funnel, and washed with brine (30 ml), where upon the organic layer was dried ($Na_2SO_4$).

When concentrated in vacuo 7 was obtained as a colourless oil, which was used directly for the next step. $R_f$=0,57 (silicagel, ether)

Step f

Preparation of 1-(S)-2-oxa-3-oxo-6R-[3R-(2-tetrahydropyranyloxy)-5-phenyl-1-pentyl-7R-(2-tetrahydropyranyloxy)-cis- bicyclo-[3,3,0]-octane 8:

The above lactone 7 (5,5 g, 11,7 mmol) was dissolved in THF (100 ml) and stirred under hydrogen atmosphere for 4 h (TLC monitoring) in the presence of Pd-C catalyst (2,1 g). Filtration through celite pad followed by concentration gave pure 8 as a colourless oil which was used directly for the next step. Yield 5,3 g (97%) ; $R_f$=0,55 (silicagel, EtoAc) $^1$H-NMR($CDCl_3$/TMS): $\sigma$=4,6(m, 1H), 4,9(m, 1H), 7,2(m, 5H).

Step g

Preparation of 1-(S)-2-oxa-3-hydroxy-6R-[3R-(2-tetrahydropyranyloxy)-5-phenyl-1-pentyl]-7R-(2-tetrahydropyranyloxy)-cis-bicyclo-[3,3,0]-octane 9:

To a stirred solution of the above lactone 8 (5,5 g, 11,7 mmol) in dry toluene (60 ml) at −78° C. was added a solution of diisobutylaluminium hydride (1,5M in toluene. 2,0 g, 14,0 mmol) dropwise. After stirring for 2 h (TLC monitoring) the reaction mixture was quenched by addition of methanol (60 ml). The temperature was raised to room temperature and stirring continued for 3–4 h. After filtration, the filtrate was concentrated in vacuo. The corresponding lactol 9 was obtained as a colourless oil. Yield 3,8 g (76%); $R_f$=0,42 (silicagel, EtoAc)

Step h

Preparation of 13,14-dihydro-17-phenyl-18,19,20-trinor-$PGF_{2\alpha}$ 10:

Sodium methylsulfinylmethide (4,1 g, 40,9 mmol) freshly prepared from sodium hydride and DMSO was added dropwise to a solution of 4-carboxybutyl triphenylphosphonium bromide (5,5 g, 20,5 mmol) in DMSO (40 ml). To the resultant red solution of ylide was added dropwise a solution of the lactol 9 (2,3 g, 5,9 mmol) in DMSO (15 ml) and the mixture was stirred for 1 h (TLC monitoring). The reaction mixture was diluted with ice and water (50 ml), acidified with 1N HCl and extracted with ethyl acetate, where upon the organic layer was dried over ($Na_2SO_4$), and concentrated in vacuo furnishing 10 as a slightly yellow oil which is used directly for the next step.

$R_f$=0,38 (silicagel, EtoAc)

Step i

Preparation of 11,15-bistetrahydropyranyloxy-13,14-dihydro-17-phenyl-18,19,20-trinor-$PGF_{2\alpha}$-ipr ester 11:

To a stirred solution of the crude product 10 (3,27 g, 5,9 mmol) in acetone (25 ml) at ±0° C., was added DBU (6,25 g, 41.0 mmol) dropwise, and the mixture was allowed to warm up to room temperature, followed by dropwise addition of isopropyliodide (7,3 g, 35,2,mmol) with continuously stirring for 4 h (TLC monitoring). The mixture was transferred to a separatory funnel, diluted with ether (100 ml), washed with brine (30 ml), citric acid 3% (2×25 ml) and sodium hydrogen carbonate 5% (2×25 ml), dried ($Na_2SO_4$) and evaporated. After flash column chromatography (silicagel, ether) the corresponding ester 11 was obtained as a colourless oil.

Yield=2,0 g (57%) R$_f$=0,58 (silicagel, ether) IR (neat)=V=3521, 2939, 2870, 2327, 1730, 1685, 1454, 1352, 1246, 1201, 1111, 1024. $^1$H-NMR(CDCl$_3$/TMS):σ=4,6(m,1H), 5,0(m,2H), 5,4(m,2H), 7,2(m, 5H)

Step j

Preparation of 13,14-dihydro-17-phenyl-18,19,20-trinor PGF2α isopropyl ester 12:

To a stirred solution of the above ester 11 (1.97 g,3,25 mmol) in ethanol (25 ml) was added pyridinium-4-toluenesulfonate (0,1 g, 0,33 mmol) and the mixture was warmed to 50° C. over a period of 3 h at which time the reaction was complete (TLC monitoring). The mixture was concentrated in vacuo, the residue diluted with ethyl acetate (40 ml), washed with water (20 ml) and thereafter brine (20 ml). The organic layer was dried and after flash chromatography (silicagel, ethyl acetate) the pure product 12 was obtained as a colourless oil. Yield=1,1 g(78%) R$_f$=0,24 (silicagel, EtoAc) [α]$_D^{20}$+42,32 (C=0,6 CH$_3$CN) IR (neat)=V=3387, 3060, 3024, 2978, 2932, 2863, 2361, 2346, 1728, 1653, 1603, 1560, 1507, 1497, 1453, 1438, 1374, 1311, 1248, 1181, 1146, 1109, 1029, 967, 820, 747, 723, 700, 665. $^1$H-NMR(CDCl$_3$/TMS): σ=1,2(d, 6H), 1,6-1,9(m, 10H), 2,3(t, 4H), 2,6-2,9(m, 4H), 3,65 (m, 1H), 3,9 (m, 1H), 4,2 (m, 1H), 5,0(m, 1H), 5,4(m, 2H), 7,2(m, 5H).

Step t

10. Preparation of 11,15-bistetrahydropyranyloxy-13,14-dihydro-17-phenyl-18,19,20-trinor-PGE$_2$-isopropyl ester 21

To a stirred solution of the adore bistetrahydropyranylether 11 (1,0 g, 1,66 mmol) in dichloromethane (10 ml) was added pyridinium chlorochromate (1,4 g, 6,66 mmol) adsorbed on alumina. After completion of the reaction ether (50 ml) was added, the product filtered, and washed with ether (50 ml). The ether layer was washed with sodiumhydrogencarbonate 5% (2×30 ml), dried on Na$_2$SO$_4$ and evaporated in vacuo. The crude product was subjected to flash chromatography (silica gel, ether) furnishing 21 as a colourless oil; yield=43%.

Step u

11. Preparation of 13,14-dihydro-17-phenyl-18,19,20-trinor PGF$_2$-isopropyl ester 22.

To a stirred solution of The above ester 21 (0,4 g, 0,67 mmol) in ethanol, was added pyridinium-4-toluenesulfonate <16,8 mg, 0,07 mmol) and the mixture was warmed to 50°-55° C. over a period of 3 h at which time the reaction was completed (TLC monitoring). The mixture was concentrated in vacuo, the residue diluted with ethyl acetate (50 ml), washed with water (20 ml) and thereafter brine (20 ml). The organic layer was dried and after flash chromatography (silica gel, ethylacetate: ether 2:1), the pure product 22 was obtained as a colourless oil; yield=78%.

R$_f$=0,31 (silica gel, ethylacetate) $^1$H-NMR(CDCl$_3$/TMS): delta=1,2 (6H d), 3,6 (1H m), 4,1 (1H m), 5,0 (1H m), 5,3 (2H m), 7,2 (5H m)

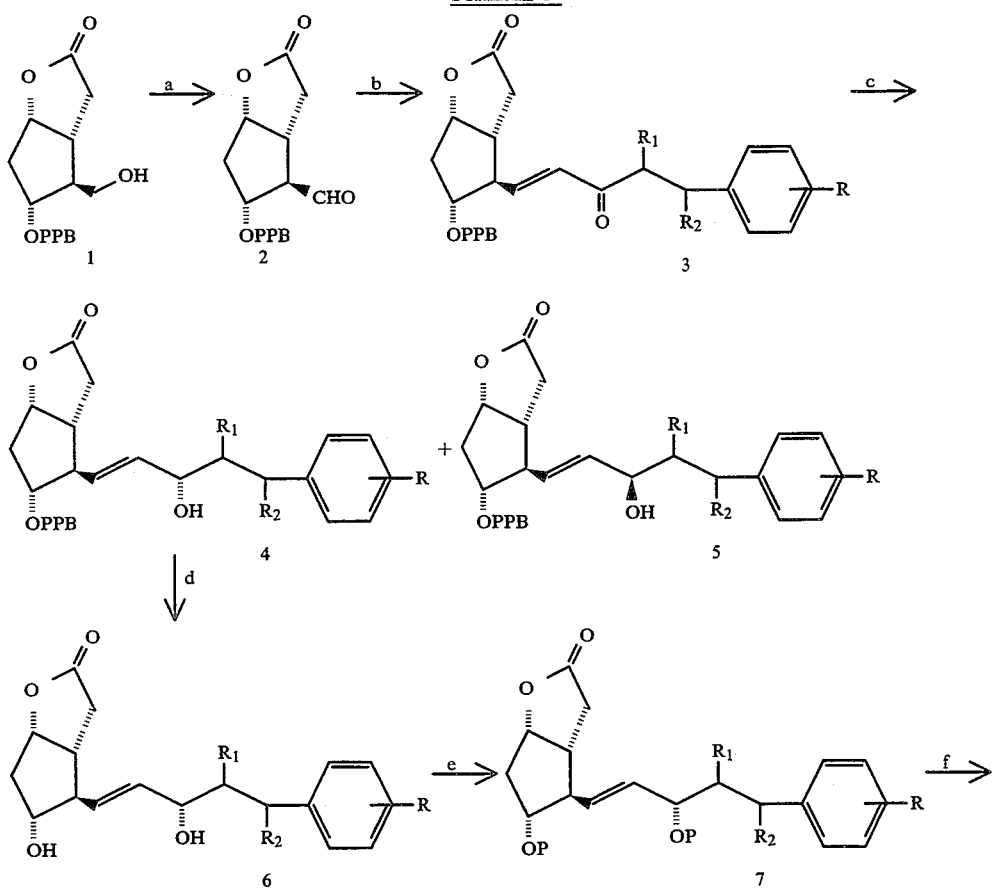

SCHEME 1

5,359,095
SCHEME 1
-continued
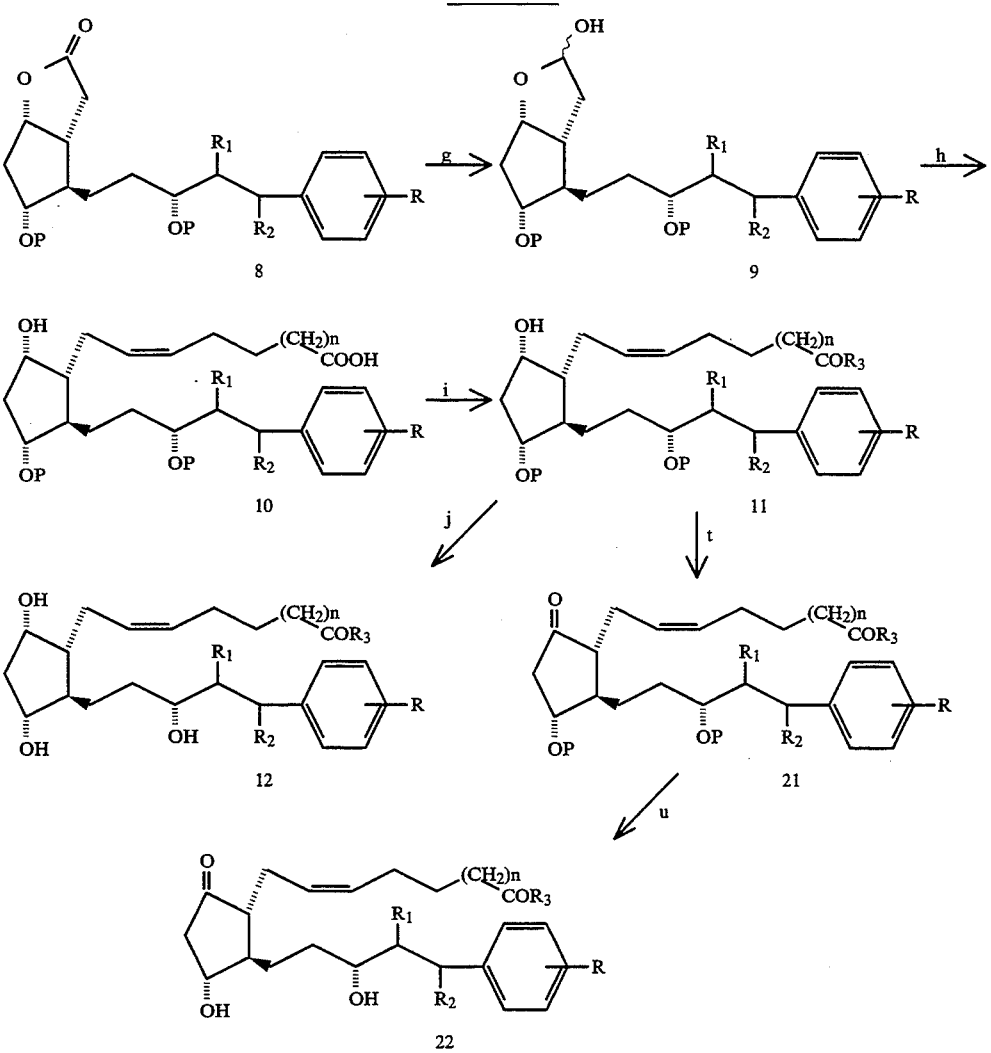
SCHEME 2
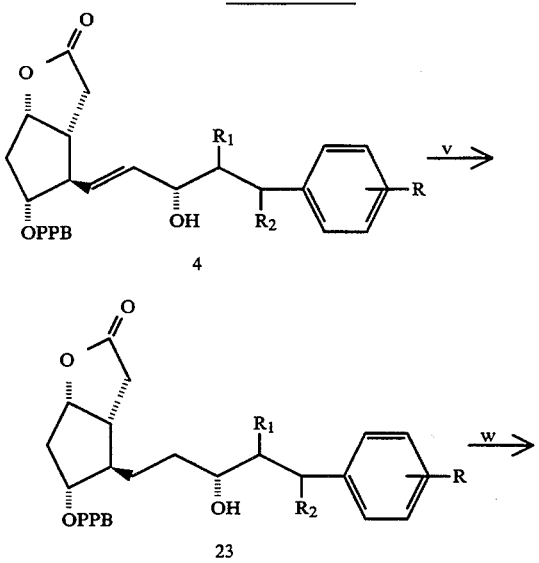

-continued
SCHEME 2

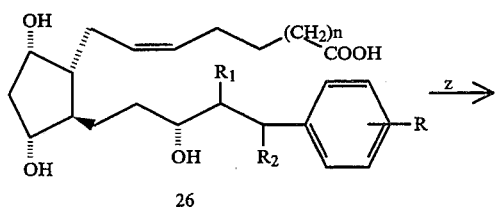

26

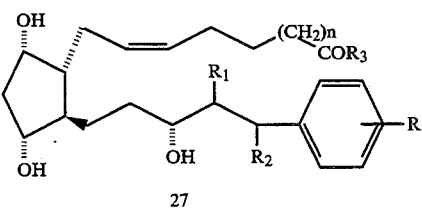

27

REFERENCES

1. K. Crawford, P. L. Kaufman and B. A. True Gabel. Invest. Ophthalmol. Vis. Sci.(1987) 11.
2. S. F. E. Nilsson, J. Stjernschantz and A. Bill. Invest. Ophthalmol. Vis. Sci.(1987) 284.
3. L. Z. Bito, A. Draga, D. J. Blanco and B. Camras. Invest. Ophthalmol. vis. sci. (1983) 312–319.
4. E. J. Corey, Zdenek Arnold and Jonathan Hutton. Tetrah. Lett. 4 (1970) 307–310.
5. K. E. Pfitzner and J. G. Mofatt. J. Am. Chem. Soc. 87 (1965) 5670–5678.
6. H. C. Brown and S. Krishnamurthy. J. Am. Chem. Soc. 94 (1972) 7159–7161.
7. U.S. Pat. No. 4,739,078.
8. E. J. Corey and G. T. Kwiatkowski J. Amer. Chem. Soc. 88 (1966) 5654.
9. M. C. Dart and H. B. Henbest Nature 183 (1959) 817.
10. M. C. Dart and H. B. Henbest J. Chem. Soc. 3 (1960) 3563.

I claim:

1. Method for preparing 13,14-dihydro-17-phenyl analogues of $PGF_{2\alpha}$ or $PGE_2$ which comprises reacting the compound (4)

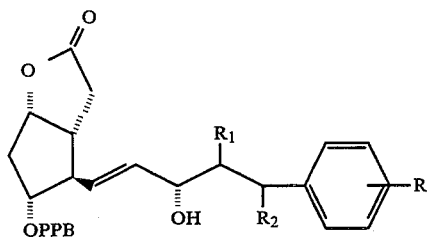

by basic hydrolysis to give the compound (6)

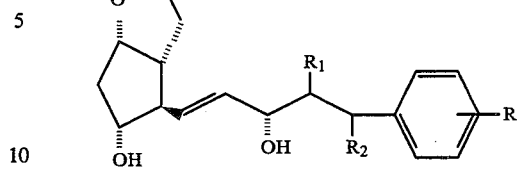

which is thereafter provided with a protecting group to protect the hydroxyl groups to give the compound (7)

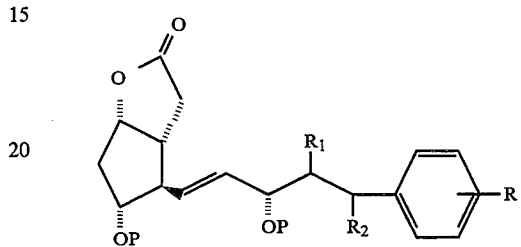

which is reduced under hydrogen atmosphere to give the compound (8)

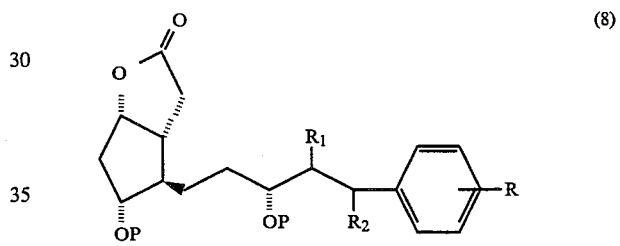

wherein
R is hydrogen or a halogen, hydroxyl, cyanide, alkyl, hydroxyalkyl, or trifluoromethyl, on the aromatic ring,
$R_1$ and $R_2$ are each hydrogen, alkyl, hydroxyl, halogen or hydroxyalkyl substituents,
P is a protecting group, and
PPB is para phenyl benzoyl.

2. The method which comprises the steps of removing the phenylbenzoyl group in 1-(S)-2-oxa-3-oxo-6R-[3S-hydroxy-5-phenyl-1-trans-pentenyl]-7R-(4-phenylbenzoyloxy)cis-bicyclo-[3,3,0]-octane by hydrolysis to give the compound 1-(S)-2-oxa-3-oxo-6R-[3S-hydroxy-5-phenyl-1-trans-pentenyl]-7R-hydroxy-cis-bicyclo-[3,3,0]octane which is thereafter provided with a protecting group to protect the hydroxyl groups to give the compound 1-(S)-2-oxa-3-oxo-6R-[3S-(2-tetrahydropyranyloxy)-5-phenyl-1-trans-pentenyl]-7R-(2-tetrahydropyranyloxy)) -cis-bicyclo-[3,3,0]-octane which is reduced under a hydrogen atmosphere to give the compound 1-(S)-2-oxa-3-oxo-6R-[3S-(2-tetrahydropyranyloxy)-5-phenyl-1-pentyl]-7R-(2-tetrahydropyranyloxy) -cis-bicyclo-[3,3,0]-octane.

* * * * *